United States Patent [19]

Tanimoto et al.

[11] Patent Number: 4,645,342

[45] Date of Patent: Feb. 24, 1987

[54] METHOD OF LASER EMISSION SPECTROSCOPIC ANALYSIS OF STEEL AND APPARATUS THEREFOR

[75] Inventors: Wataru Tanimoto; Kouzou Tsunoyama, both of Chiba, Japan

[73] Assignee: Kawasaki Steel Corp., Hyogo, Japan

[21] Appl. No.: 682,897

[22] Filed: Dec. 18, 1984

[30] Foreign Application Priority Data

Oct. 5, 1984 [JP] Japan .................................. 59-209096

[51] Int. Cl.[4] ............................................ G01N 21/63
[52] U.S. Cl. ..................................... 356/318; 356/307
[58] Field of Search ............... 356/306, 307, 313, 317, 356/318, 326, 417

[56] References Cited

U.S. PATENT DOCUMENTS

| | | | |
|---|---|---|---|
| 3,669,546 | 6/1972 | Virloget | 356/313 |
| 4,182,574 | 1/1980 | Quillfeldt | 356/318 |
| 4,191,475 | 3/1980 | Sourrouille | 356/318 |

FOREIGN PATENT DOCUMENTS

| | | | |
|---|---|---|---|
| 2336635 | 1/1974 | Fed. Rep. of Germany | 356/318 |
| 160523 | 8/1983 | Democratic Rep. of Germany. | |
| 0100323 | 6/1982 | Japan | 356/318 |
| 772250 | 4/1957 | United Kingdom | 356/307 |
| 912882 | 12/1962 | United Kingdom | 356/306 |

OTHER PUBLICATIONS

Adrain et al., Conference: Electro-Optical Laser International, Brighton, England, Mar. 25-27, 1980, p. 375.
Watson et al., J. Phys. E., vol. 10, No. 12, Dec. 1977, p. 1227.
Gibson et al., J. Phys. D.: Appl. Phys, vol. 4, No. 10, 1971, p. 1527.
"Chemical Synamics of a Laser Microprobe Vapor Plume in Controlled Atmosphere," Applied Spectroscopy, Vol. 38, No. 6, 1984.
Patent Abstracts of Japan, Vol. 4, No. 24 (E-126), Feb. 9, 1980, 54-162597.
Patent Abstracts of Japan, Vol. 8, No. 75 (P-266) [1512], Apr. 7, 1984, 58-219440 and 58-219438.

Primary Examiner—F. L. Evans
Assistant Examiner—Joel L. Harringa
Attorney, Agent, or Firm—Parkhurst & Oliff

[57] ABSTRACT

When a light emitted during the irradiation by a laser beam onto the surface of steel is spectrally separated and elements contained in the steel are analyzed quantitatively:

an infrared pulse laser beam irradiates a sample such that an energy density on the surface of the sample becomes $2.0 \times 10^9$ W/mm$^2$ or more, so that a satisfactory emission spectrum can be obtained; a light emitted from the surface of the sample is received through a path held under an atmosphere of inert gas by a light introducing system at a solid angle of 16 degrees or more, and thereafter, caused to form its image at an inlet slit of a spectroscope so that an emission spectrum intensity being low in variations can be obtained for a long period of time; and out of light emitted from the surface of the sample immediately after the irradiation by the laser beam, a firstly emitted light generating white noise is excluded and a subsequently emitted light is quantitatively analyzed, so that the accuracy of analysis can be improved with the influence of the white noise being avoided.

7 Claims, 15 Drawing Figures

METHOD OF LASER EMISSION SPECTROSCOPIC ANALYSIS OF STEEL AND APPARATUS THEREFOR

BACKGROUND OF THE INVENTION

1. Field of the Invention

This invention relates to a method of laser emission spectroscopic analysis of steel and an apparatus therefor, and more particularly to improvements in a method of laser emission spectroscopic analysis of steel and an apparatus therefor, wherein a light emitted when a laser beam irradiates the surface of steel is spectrally separated and elements contained in the steel are analyzed quantitatively and which are suitable for use in direct quantitative analysis of impurity elements in the steel such as hot metal, molten steel, slag and the like in a pig iron production process and a steel production process.

2. Description of the Prior Art

With the recent progress of the laser technique in various fields, attempts have been made to utilize lasers as a source of excitation for spectroscopic analysis. More specifically, when a powerful laser beam adapted to focus on the surface of a sample by a focusing lens having a suitable focal length irradiates the surface of the sample, a surface layer is rapidly heated. Particularly, if the laser beam is formed into pulse shapes of several tens of nanoseconds, then such conditions occur that energy is locally poured into the sample before heat is diffused in the sample, whereby melting and evaporation occur. Vapor is further excited by the laser beam to be formed into plasma which emits a light. According to the method of laser emission spectroscopic analysis, this light emitted from the plasma is transmitted to a spectroscope by means of a suitable light introducing system, spectrally separated by a diffraction grating or the like and formed into spectra, and thereafter detected by a photographic film, a photomultiplier tube, a photodiode or the like, whereby the contents of target elements are determined.

However, heretofore, a ratio between the intensity of a signal and the background (hereinafter referred to as "S/B ratio") has been very low and the variations in the output intensity of lasers have been high, whereby the accuracy of analysis and the exactness have been considerably low. Furthermore, when the method of laser emission spectroscopic analysis is used in practical process analysis or the like on site, there have been such disadvantages that mirrors in a focusing system are contaminated and so on by gases from the surface of the sample and scattered matters after the irradiation by the laser, and the method has not been practiced yet.

Aiming at making this laser emission spectroscopic analysis practicable, the applicant has proposed in Japanese Patent Laid-Open No. 100323/82 a method wherein, excluding white noises immediately after the irradiation by the laser, subsequent line spectra are integrated to improve the accuracy of analysis. However, the intensity of white noise is higher than the line spectrum intensity, and consequently, if a satisfactory intensity would not be given to the line spectra, then effective improvements in accuracy would not be attained.

Furthermore, the applicant has proposed in Japanese Patent Laid-Open No. 76744/83 a method wherein an infrared pulse laser beam irradiates a sample such that an energy density on the surface of the sample becomes $2.0 \times 10^9$ W/mm$^2$ or more. However, unless a light emitted by the laser is efficiently and sufficiently taken in, the significance has been low.

Further, the applicant has proposed in Japanese Patent Laid-Open Nos. 114746/81 and 219440/83 that mode control of a laser output and signal processing are effected so as to improve the accuracy. Likewise, unless the light emitted by the laser beam is sufficiently and efficiently taken in, it has been impossible to expect a satisfactory effect.

SUMMARY OF THE INVENTION

The present invention has been developed to obviate the above-described disadvantages of the prior art and has as its object the provision of a method of laser emission spectroscopic analysis of steel and an apparatus therefor. The invention is practicable and usable under an adverse environment on site. Light excited and generated by a laser beam can be caused to enter a spectroscope with a satisfactory intensity, so that the accuracy of analysis can be greatly improved by additional use of various methods of improving the accuracy which have been proposed by the applicant.

Figure 1:
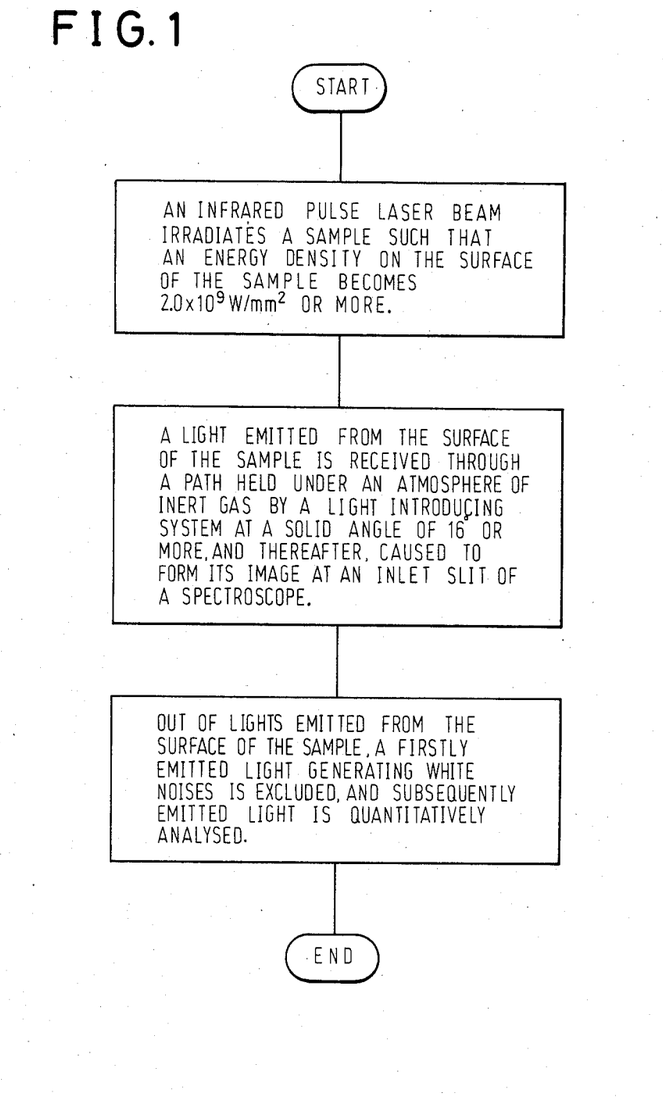
FIG. 1 is a flow chart showing a method of laser emission spectroscopic analysis of steel according to the present invention.

To this end, the present invention contemplates a laser emission spectroscopic method wherein a light emitted when a laser beam irradiates the surface of steel is spectrally separated and various elements contained in the steel are quantitatively analyzed. As the technical gist thereof is illustrated in FIG. 1, an infrared pulse laser beam irradiates a sample such that an energy density on the surface of the sample becomes $2.0 \times 10^9$ W/mm$^2$ or more, a light emitted from the surface of the sample is received by a light introducing system at a solid angle of 16 degrees or more through a path which is held under an atmosphere of inert gas, thereafter, is caused to form its image at an inlet slit of a spectroscope, and, out of light emitted from the surface of the sample immediately after the irradiation by the laser, a firstly emitted light generating white noises is excluded and a subsequently emitted light is quantitatively analyzed.

A specific form of the present invention is of such an arrangement that an output of the infrared pulse laser beam is fixed to a gauss distribution type TEM$_{00}$ mode, so that an analysis with high accuracy can be conducted in spite of variations and the like in the laser output intensity.

Another specific form of the present invention is of such an arrangement that inert gas is blown into the path of the emitted light at a flowrate of 50 l/min or more, whereby the path is held under an atmosphere of inert gas, so that, even if the sample is in the molten state, an ascending current can be reliably suppressed and sample dust generated by the irradiation of laser can be removed.

A further specific form of the present invention is of such an arrangement that, out of light emitted from the surface of the sample immediately after the irradiation by the laser, a firstly emitted light of 1.5 microsecond or less is excluded so that the firstly emitted light generating white noise can be reliably removed.

A still further specific form of the present invention is of such an arrangement that, out of the light emitted from the surface of the sample immediately after the irradiation of laser, the firstly emitted beam of 1.5 microsecond or less is excluded and a subsequently emitted beam of up to 16 microseconds is quantitatively analyzed, whereby the firstly emitted light generating the white noise is reliably removed and an unnecessary emitted light is not used for the analysis.

A still further specific form of the present invention is of such an arrangement that, in conducting the quantitative analysis, an intensity of a light having a preset wavelength emitting no spectral line is made to be a background, and the background is subtracted from an intensity of a spectral line, so that, particularly, the influence of a continuous spectrum unavoidable when a powerful pulse laser beam is used for molten steel of high temperature can be avoided.

A still further specific form of the present invention is of such an arrangement that, in conducting the quantitative analysis, an analyzed value is measured from an intensity of a spectral line of an element to be measured only when an intensity of a preset spectral line or an intensity ratio between a pair of preset spectral lines is within a preset range, so that an analyzed value with high accuracy can be obtained.

A yet further specific form of the present invention is of such an arrangement that an output from the infrared pulse laser beam is fixed to the gauss distribution type $TEM_{00}$ mode, in conducting the quantitative analysis, the intensity of the light having the preset wavelength emitting no spectral line as the background is subtracted from the intensity of the spectral line, and an analyzed value is measured from the intensity of the spectral line of the element to be measured only when the intensity of the preset spectral line or the intensity ratio between the pair of preset spectral lines is within the preset range, so that an analyzed value with very high accuracy can be obtained.

According to the present invention, the light excited and generated by the laser beam can be caused to fall into the spectroscope at a satisfactory intensity, and the additional use of the methods of improving the accuracy, which have been proposed by the applicant, makes it possible to greatly improve the accuracy of analysis, so that a practical analysis usable even under an adverse environment on the site can be conducted.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

In general, in laser emission spectroscopic analysis, a laser beam as the excitation source is focussed on and irradiates the surface of a sample, a light excited and generated is dispersed by a spectroscope, and concentrations of various elements are determined from the intensities of spectral lines of the elements.

As the laser beam for this laser emission spectroscopic analysis, a ruby laser beam having a wavelength of 0.69 micrometer is used in many cases. In this case, the laser beam is formed into pulse shapes of the width of several tens of nanoseconds by use of high speed switching (Q switching) elements such as Kerr cells, Pockels cells or the like, and a portion irradiated by the laser is changed into the high energy state before thermal energy is diffused around the portion irradiated by the laser.

The inventors planned to conduct the above-described laser emission spectroscopic analysis by use of an infrared pulse laser beam further excellent in the heat transfer rate, caused an infrared pulse laser having a wavelength of 1.06 micrometer emitted from an Nd glass laser to irradiate the surface of steel, and observed an emission spectrum. As the result, the inventors found the following.

(1) The emission spectrum having a satisfactorily excellent S/B ratio is obtainable without using an auxiliary electrode.

Figure 2:
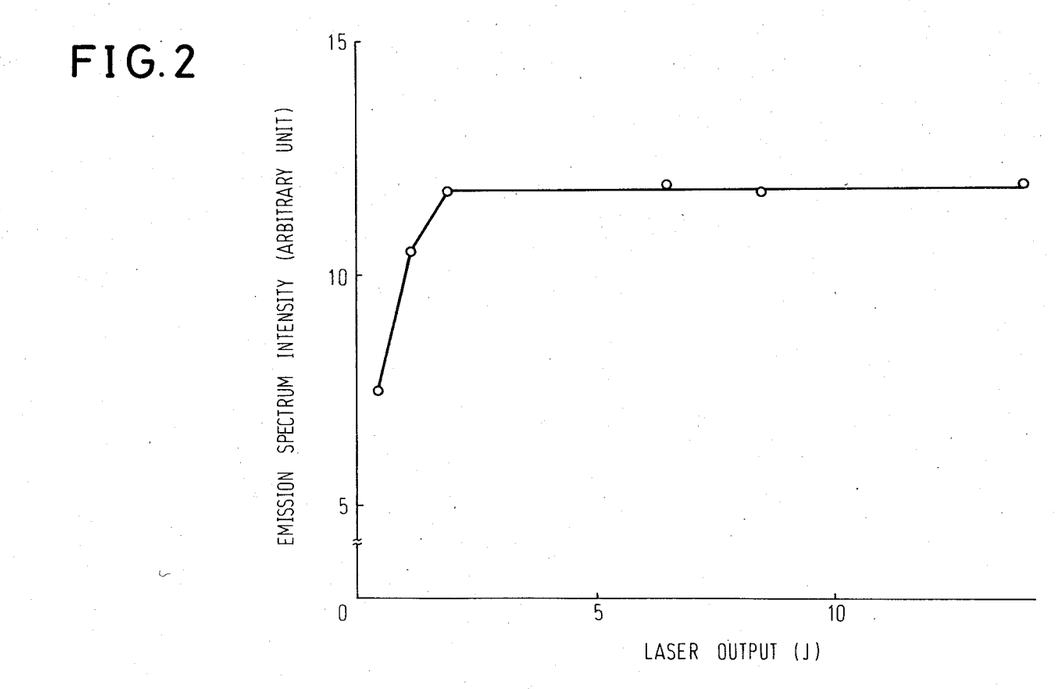
FIG. 2 is a graphic chart showing the relationship between the laser output and the emission spectrum intensity in a method of the present invention.

(2) The intensity of the emission spectrum increases with the increase in the laser output, but has a trend to be saturated in time as shown in FIG. 2.

Figure 3:
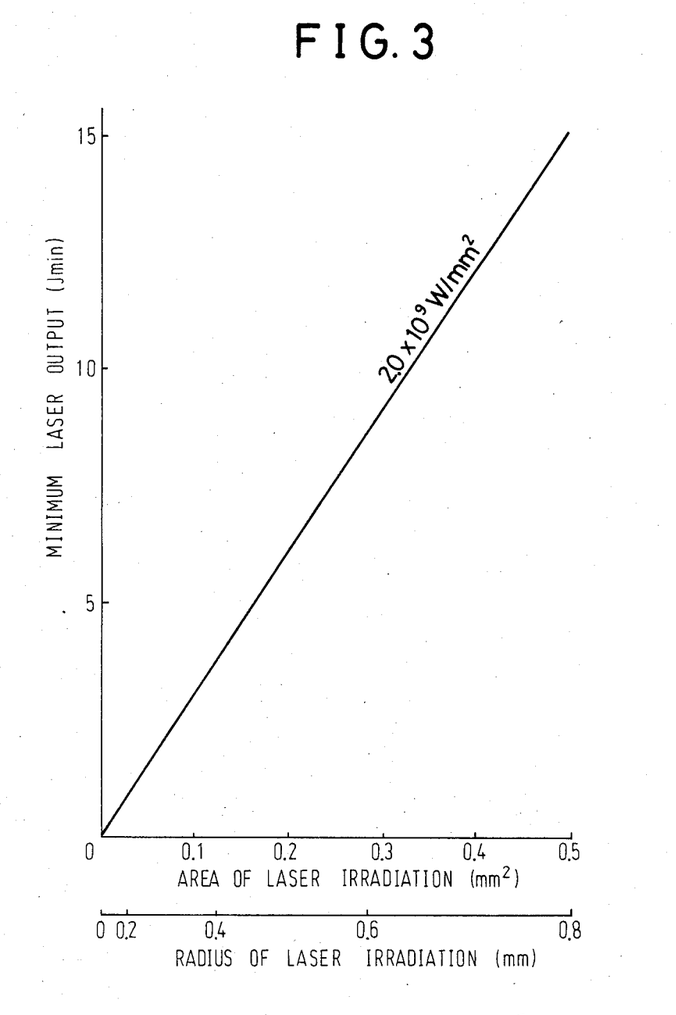
FIG. 3 is a graphic chart showing the relationship between area of the irradiation by the laser on the surface of the sample and the first laser output whose spectrum intensity reaches a saturated value in a method of the present invention.

(3) A rectilinear relationship shown in FIG. 3 is established between the area of the irradiation by the laser on the surface of the sample and the first laser output J min, under which the emission spectrum intensity reaches the saturated value. Additionally, during the experiments, the pulse width of the laser beam is made to be 15 nanoseconds and the position of the focusing lens is moved, whereby the area of irradiation by the laser is varied. It is apparent from FIG. 3 that, if an output density of $2.0 \times 10^9$ W/mm$^2$ or more is obtained, then a satisfactorily good emission spectrum can be obtained.

Figure 4:
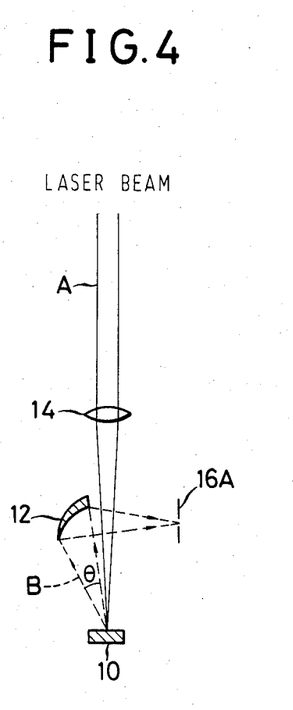
FIG. 4 is an arrangement drawing showing the basic arrangement of the apparatus for laser emission spectroscopic analysis in a method of the present invention.
Figure 5:
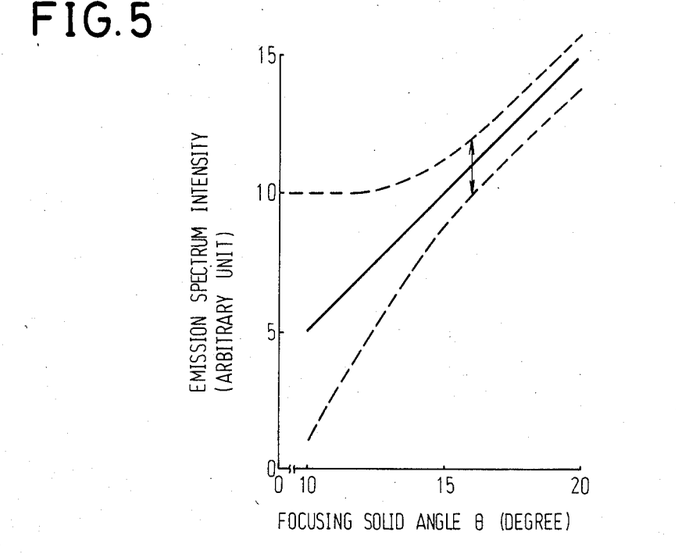
FIG. 5 is a graphic chart showing the relationship between the focusing solid angle $\theta 0$ and the emission spectrum intensity in a method of the present invention.
Figure 6:
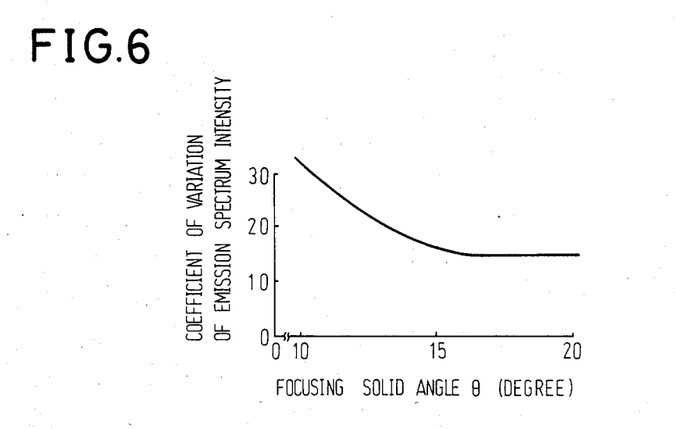
FIG. 6 is a graphic chart showing the relationship between the focusing solid angle and the coefficient of variation of the emission spectrum intensity in a method of the present invention.

Subsequently, the inventors changed the area of a focusing mirror (concave mirror) 12 for receiving an emitted light B excited and generated in an apparatus having the arrangement shown in FIG. 4, in which an energy density of a laser beam A on the surface of the sample (10) is made to be $2.0 \times 10^9$ W/mm$^2$, and observed the changes in the spectrum intensity when the focusing solid angle $\theta$ is changed. In FIG. 4, designated at 14 is a focusing lens and 16A an inlet slit of a spectroscope. FIG. 5 shows the results of experiments. In FIG. 5, broken lines show the width of variations of the emission spectrum intensity obtained by ten measurements. As apparent from FIG. 5, the variations in the emission spectrum intensity shrink with the increase in the focusing solid angle $\theta$. FIG. 6 shows the relationship between the coefficient of variation (one obtained by dividing a standard deviation by a mean value) of the emission spectrum intensity in FIG. 5 and the focusing solid angle $\theta$. It is found from FIG. 6 that the coefficient of variation is reduced with the increase of the focusing solid angle $\theta$, but becomes constant when the solid angle $\theta$ is 16 degree and thereafter. In consequence, it is found that if the solid angle $\theta$ is 16 degree or more, an emission spectrum intensity low in variations is obtainable.

Figure 7:
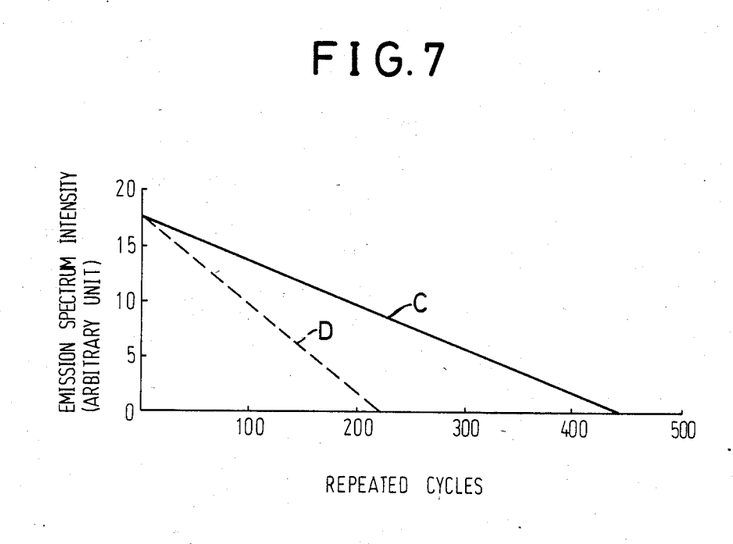
FIG. 7 is a graphic chart showing the relationship between the repeated cycles of analysis and the changing conditions of the emission spectrum intensity in a method of the present invention.

However, in the case of the apparatus having the construction shown in FIG. 4, if the apparatus is used for a long period of time, dust of the sample scattered by the irradiation by the laser adheres to the focusing lens 14 of a laser beam A and the surface of the focusing mirror 12 of emitted light B, whereby they may be damaged or the light intensity may be lowered. Particularly, when the sample is in a molten state, an ascending current is generated, and the influence thereof is notable. FIG. 7 shows the changing conditions of the emission spectrum intensity when the apparatus shown in FIG. 4 is used for a long period of time. In the drawing, a solid line C shows the case of analyzing only a solid sample and a broken line D shows the case of analyzing a molten sample.

Figure 8:
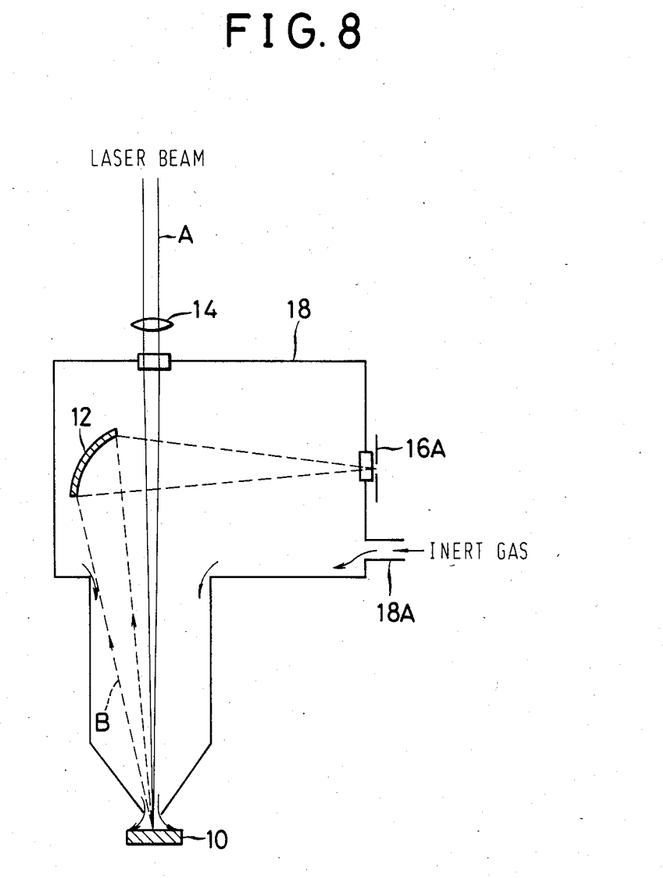
FIG. 8 is an arrangement drawing showing the basic arrangement of the apparatus for laser emission spectroscopic analysis, to which is added a casing for holding the sample beam path under an atmosphere of inert gas in accordance with the present invention.
Figure 9:
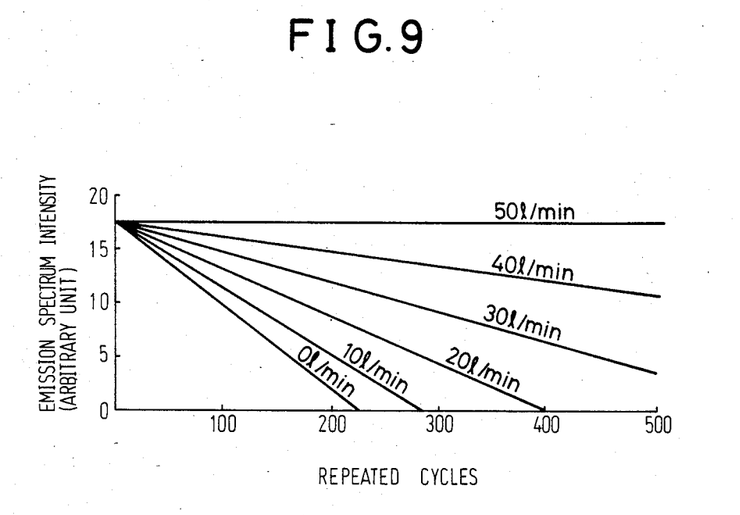
FIG. 9 is a graphic chart showing the relationship between the repeated cycles of analysis and the emission spectrum intensity in the apparatus shown in FIG. 8.

Then, the inventors modified the apparatus such that the apparatus is covered by a case 18 and inert gas is blown into the case 18 through an inert gas introducing port 18A as shown in FIG. 8. FIG. 9 shows the changing conditions of the emission spectrum intensity when only the molten sample is analyzed for a long period of time while inert gas is blown into the apparatus shown in FIG. 8 through the inert gas introducing port 18A. In the drawing, numerical values indicate the flowrates of the inert gas. As apparent from FIG. 9, if the inert gas having a flowrate of 50 l/min or more is caused to flow, then the ascending current can be suppressed even if the sample is in the molten state, and the dust of the sample generated by the irradiation by the laser can be removed. Furthermore, the emission light path is purged by this inert gas, so that a vacuum ultraviolet light can be prevented from being absorbed by oxygen in the air.

Figure 10:
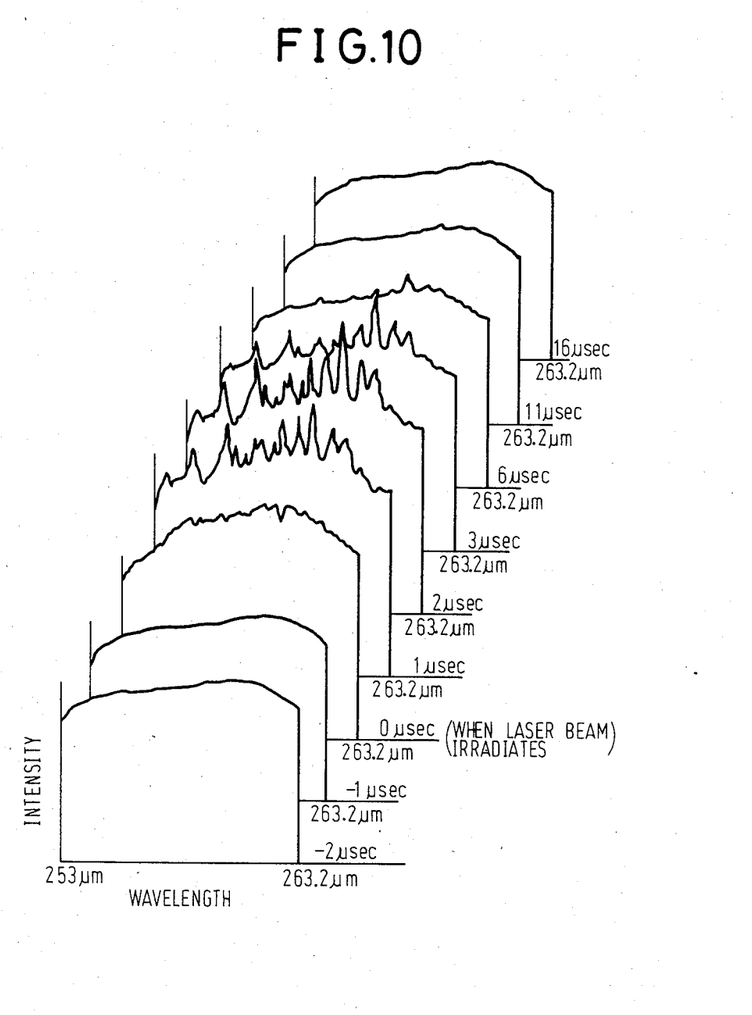
FIG. 10 is a graphic chart showing an Fe spectrum in the proximity of the wavelength 258 nanometers between 2 microseconds before the irradiation by the laser to 16 microseconds after the irradiation by the laser.
Figure 11:
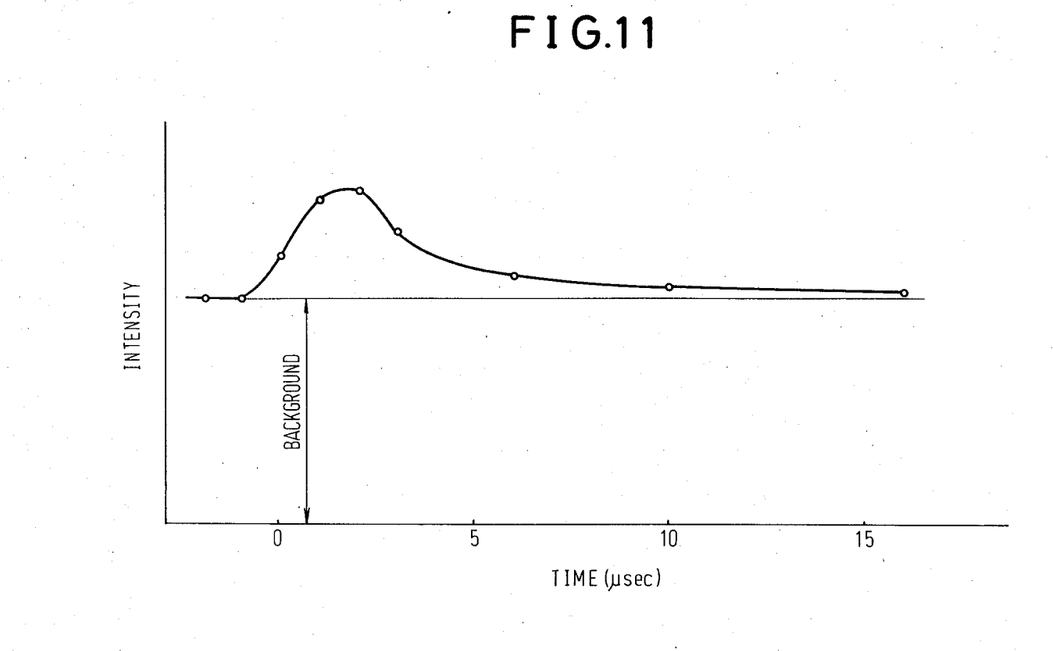
FIG. 11 is a graphic chart showing the changing conditions of the intensity of an Fe spectrum having a wavelength of 259.8 nanometers as shown in FIG. 10.

Further, the inventors caused an infrared laser beam having a wavelength of 1.06 micrometer in a pulse shape of a width of about 10 nanoseconds to irradiate the surface of Fe so as to convert part of the Fe into plasma, measured an Fe spectrum every 1 microsecond in the proximity of a wavelength of 258 nanometers from a light emitted by the plasma from 2 microsecond before the irradiation by the laser to 16 microsecond after the irradiation by the laser, and obtained the results shown in FIGS. 10 and 11. FIG. 10 shows the relationship between the wavelength and the light intensity, and FIG. 11 shows the changes with time of the line spectrum intensity of Fe having a wavelength of 259.8 nanometers as shown in FIG. 10. From the results of experiments, the inventors have found that a continuous light (white noise) as the background is emitted for about 1.5 microsecond from the irradiation by the infrared pulse laser, the line spectrum by atoms and univalent ions, which are used in the spectroscopic analysis hardly appears for about 1.5 microsecond from the irradiation by the laser, but is observed for 15 microsecond upto 16 microsecond after a lapse of about 1.5 microsecond upon the irradiation by the laser.

To put together the above-described data, it may be concluded that, by taking the following measures, a practical laser emission spectroscopic analysis can be conducted under the environment on the site.

(1) The energy density of the laser beam on the surface of the sample is made to be $2.0 \times 10^9$ W/mm$^2$ or more.

(2) The focusing solid angle $\theta$ is made to be 16 degree or more.

(3) The emitted light path is held under an atmosphere of the inert gas.

(4) White noise for 1.5 microsecond immediately after the irradiation of laser beam is excluded, and the subsequent emitted light is quantitatively analyzed.

Further, the inventors have found that, in conducting the above-described laser emission spectroscopic analysis, additional use of the method of fixing the laser beam to the mode, which has been proposed in Japanese Patent Laid-Open No. 219440/83 by the applicant, and of the method of removing the background, which has been also proposed in Japanese Patent Laid-Open No. 114746/81 by the applicant, makes it possible to greatly improve the accuracy.

More specifically, the following are made clear by the survey of the inventors.

(1) If an output from a laser oscillator is increased, then the coefficient of variation of the spectral line intensity decreases. However, an amplifier is provided at a stage posterior to the laser oscillator and, if an output thereof is further increased, then the coefficient of variation increases.

(2) Even when the laser beam is obtained only by use of the laser oscillator without using the amplifier, the variation of the spectral line intensity is higher than the variation of the laser output.

Figure 12:
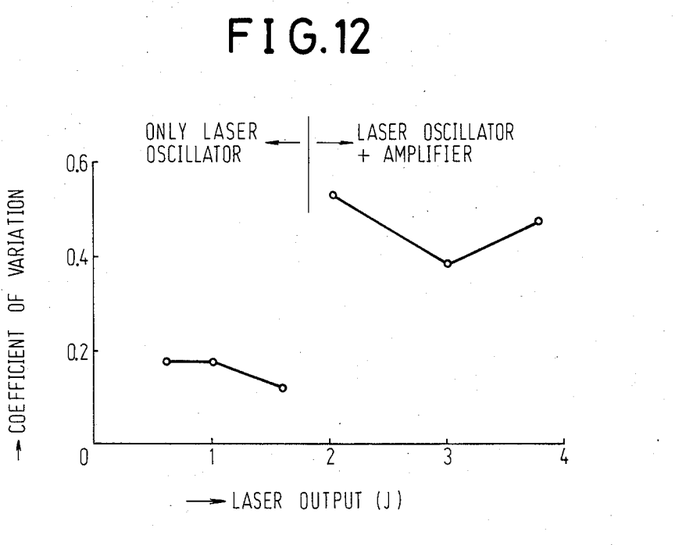
FIG. 12 is a graphic chart showing the relationship between the laser output and the coefficient of variation of the intensity of an Fe spectrum having a wavelength of 271.4 nanometers.
Figure 13:
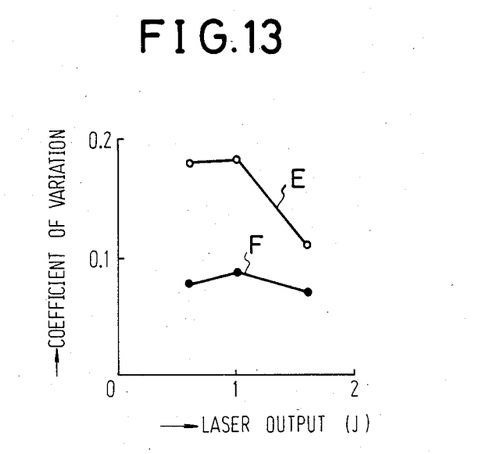
FIG. 13 is a graphic chart showing the relationship between the laser output, the coefficient of variation of the laser output and the coefficient of variation of the intensity of the spectral line of Fe having a wavelength of 271.4 nanometers.

FIGS. 12 and 13 show the results of experiments. The sample used in the experiments is an Fe alloy, and, as the laser beam, an infrared laser beam having a wavelength of 1.06 micrometer and a pulse width of 15 nanoseconds is used. As apparent from FIG. 12, when the laser output becomes an output 2 joule or more with an amplifier being utilized, the coefficient of variation suddenly increases. The cause seems to reside in the intensity distribution of the laser pulses. Namely, in general, there are various symmetries in the intensity distribution (mode) in the direction of the vertical section of the laser beam emitted from a laser oscillator. When such a high output is required as used in the emission spectroscopic analysis, multi-mode oscillation, in which the mode is varied with every pulse, is adopted. However, when several peaks of the intensity distribution are present in a beam as described above, if an amplifier is actuated, then a specified peak is amplified preferentially. In consequence, if a laser beam having the above-described intensity distribution is converged onto the surface of the sample, then, within this spot caliber, a local area, which is high in laser irradiation density, is generated. Such wide fluctuations in the irradiation density as described above vary with every pulse, whereby the emission spectrum intensity is subjected to the variations. Then, the inventors thought of fixing the laser used in the emission spectroscopic analysis to $TEM_{00}$ mode, from which the gauss distribution type output can be obtained, by utilizing the mode lock technique used in holography and the like. As the mode, $TEM_{01}$ mode or the like, from which an annular distribution can be obtained, may be adopted except the above-described mode, however, the gauss distribution seems optimal to the emission spectroscopic analysis. Additionally, if the mode lock is effected, the laser output decreases, however, this decrease can be made up for by an increase in the output of the laser oscillator and use of an additional amplifier. Needless to say, when the laser beam is fixed to $TEM_{00}$ mode, the mode will not be changed even if an amplifier is used.

On the other hand, FIG. 13 shows a comparison between the coefficient of variation (solid line E) of a spectral line intensity of Fe having a wavelength of 271.4 nanometers and the coefficient of variation (solid line F) of the laser output when the same laser beam as shown in FIG. 12 irradiates an Fe alloy. In spite of the fact that no amplifier is used, the change in the spectral line intensity is higher than the width of variations of the laser output. The above-described change in the emission spectrum intensity is tolerably improved by the mode lock; however, in addition thereto, the influence of the wide fluctuations in the evaporation and excitation processes, which occur on the surface of the sample during the irradiation by the laser cannot be disregarded. Since the latter cannot be removed only by controlling the laser output and the mode, as the preset spectral line or lines, which can be obtained during the irradiation by the laser, one or two Fe spectral lines each having a suitable wavelength are selected in the exemplary case of an Fe alloy, an intensity of the preset spectral line or an intensity ratio between the two preset spectral lines is constantly monitored, and a spectral line intensity of an element to be measured is read only when the intensity or the intensity ratio is within a preset range of variations. Particularly, the latter method of regulating the intensity ratio makes it possible to restrict the temperature of plasma generated by the irradiation by the laser, thus proving effective in improving the accuracy of analysis.

Figure 14:
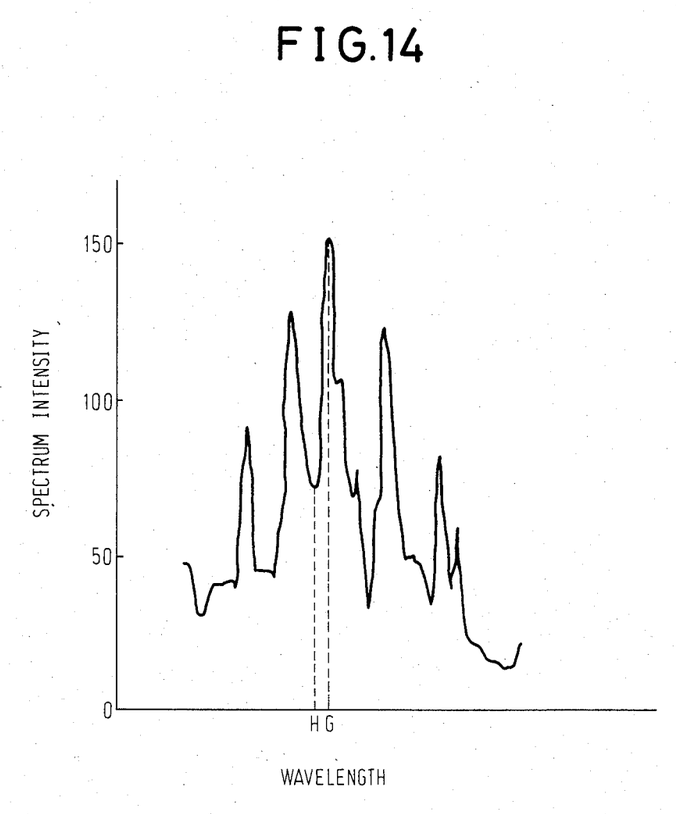
FIG. 14 is a graphic chart showing the waveform of the spectrum obtained through the dispersion of the light excited and generated by irradiation by the laser.

As a method to further improve the accuracy of analysis, a beam intensity having a specified wavelength emitting no spectral line as the background is subtracted from the spectral line intensity. FIG. 14 shows the results of spectrally separating a light emitted by the irradiation by the laser and of observing the spectra. In FIG. 14, a point G indicates the spectrum of the element and a point H the background emitting no spectral line. In consequence, the pure spectral line intensity is represented by a difference obtained by subtracting the intensity at the point H from the intensity at the point G. This method is also an effective one applicable to a sample in the molten state where the background intensity varies greatly.

In consequence, when the requirements of the present invention are satisfied and further the above described methods of improving the accuracy are additionally used, all the problems, which have been occurring on the site during the application, are solved and a useful accuracy of analysis can be provided.

Detailed description will hereunder be given of one embodiment of the analyzing apparatus, to which is applied the method of laser emission spectroscopic analysis of steel according to the present invention, with reference to the drawing.

Figure 15:
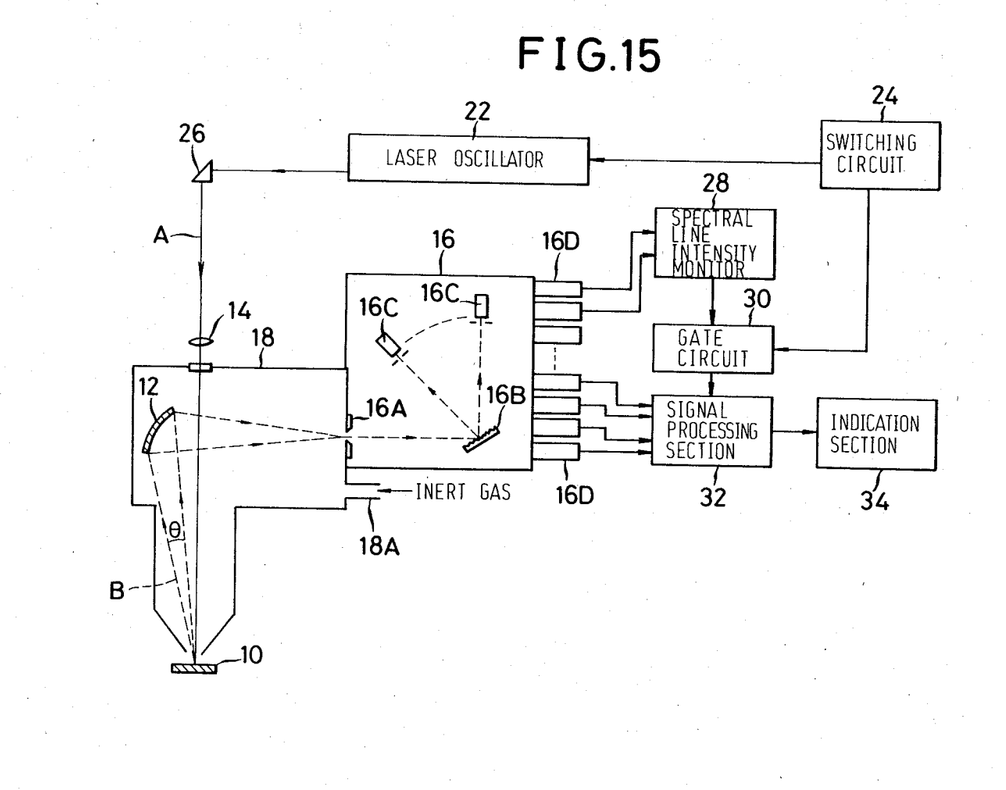
FIG. 15 is a block diagram showing the arrangement of the embodiment of an apparatus for laser emission spectroscopic analysis, adapted to use of the method of laser emission spectroscopic analysis of steel according to the present invention.

As shown in FIG. 15, this embodiment comprises:

a laser oscillator 22 assembled thereinto with a mode lock mechanism, not shown, for emitting an infrared pulse laser beam having an energy density of $2.0 \times 10^9$ W/mm$^2$ or more on the surface of a sample 10;

a switching circuit 24 for actuating a high speed switching element, not shown, assembled in the laser oscillator 22;

a rectangular prism 26 for diverting the irradiating direction of a laser beam emitted from the laser oscillator 22;

a focusing mirror (concave mirror) 12 for focusing a light emitted from the surface of the sample 10 at a focusing solid angle $\theta$ of 16 degrees or more;

a casing 18, into which is introduced inert gas for holding a path of the light emitted from the sample under an atmosphere of the inert gas, through an inert gas introducing port 18A;

a spectroscope 16 wherein the light emitted from the sample whose image is formed at an inlet slit 16A of the spectroscope by the focusing mirror 12, is spectrally separated into spectral lines by a diffraction grating 16B or the like, and the spectral lines are converted into electric signals for the target spectral lines by a group of photo electric signal transducing elements 16C;

a spectrum intensity monitor 28 for monitoring an intensity of a preset spectral line or an intensity ratio between a pair of preset spectral lines, all of which are emitted from a group of output terminals 16D of the spectroscope 16;

a gate circuit 30 to be opened during a period from 1.5 microsecond after the start of the irradiation by the laser up to 16 microseconds thereafter and when the intensity of the preset spectral line or the intensity ratio between the pair of preset spectral lines is within the preset range, so that an output from the spectroscope 16 can be adopted in the analysis;

a signal processing section 32 for obtaining an analyzed value in response to a signal inputted from the group of output terminals 16D of the spectroscope 16 when the gate circuit 30 is opened; and an indication section 34 for indicating the analyzed value obtained by the signal processing section 32.

As the laser oscillator 22, for example, a ruby laser having a wavelength of 0.69 micrometer or an infrared laser having a wavelength 1.05 to 1.06 micrometer may be used.

The rectangular prism 26 is intended to cause a laser beam A to irradiate the surface of the sample 10 at a predetermined ange, and, when a laser emitting section including the laser oscillator 22 is provided in a predetermined direction, the rectangular prism 26 may be dispensed with.

As the group of photo-electric signal transducing elements 16C, for example, a photo-diode or a photo-multiplier tube may be used.

Description will hereunder be given of action of this embodiment.

The laser beam A fixed to $TEM_{00}$ mode is emitted from the laser oscillator 22 controlled by the switching circuit 24, passed through the rectangular prism 26 and the focusing lens 14, and focused onto the surface of the sample 10. At this time, the energy density on the surface of the sample 10 is made to be $2.0 \times 10^9$ W/mm² or more.

The emitted light B excited and emitted by the laser beam is caused to form its image at the inlet slit 16A of the spectroscope 16 by the focusing mirror 12 having the focusing solid angle $\theta$ of 16 degree or more. At this time, the inert gas is blown into the light introducing system in the casing 18 through the inert gas introducing port 18A and the light introducing system is held under the atmosphere of the inert gas. The inert gas is also blown onto the surface of the sample 10.

The light introduced into the spectroscope 16 through the inlet slit 16A is diffused by ordinary means such for example as the diffraction grating 16B. Out of the spectra thus diffused, spectrum intensity or intensities (one or two) for regulating data, a base constituent element spectrum intensity $Sig_1$, a background intensity $BG_1$ thereof, a measured element spectrum intensity $Sig_2$ and a background intensity $BG_2$ thereof are converted into electric signals by the group of photo-electric signal transducing elements 16C and outputted to the group of output terminals 16D.

Out of the above-mentioned signals, the spectrum intensity signal for regulating data is delivered to the spectrum intensity monitor 28, where judgment as to whether the intensity thereof or the intensity ratio between the pair of spectral line intensities is within the preset range or not is made. In the case of being within the preset range, the gate circuit 30 is actuated, whereby the respective spectrum intensity signals for the analysis and measurement are inputted to the signal processing section 32.

At the same time, a signal is delivered to the gate circuit from the switching circuit 24 when the laser beam is oscillated. And a gate is operated, being referenced from the aforesaid signal, to exclude the emitted light for 1.5 microsecond immediately after the irradiation by the laser and to signal-process the subsequent emitted light up to 16 microseconds, out of the respective spectrum intensity signals for the analysis and measurement.

In the signal processing section 32, the spectrum intensity ratio obtained by subtracting the background therefrom $(Sig_2 - BG_2)/(Sig_1 - BG_1)$ is calculated, a concentration of the element to be measured is worked out on the basis of a calibration curve prepared in advance by use of a reference sample and indicated in the indication section 34.

The following is the coefficient of variation obtained by analyzing the concentration of contained silicon in a sample of an Fe alloy in the apparatus shown in FIG. 15 by various methods. Namely, according to the conventional method, the coefficient of variation was 11.4%. According to a first method of the present invention, wherein the energy density on the surface of the sample was made to be $2.0 \times 10^9$ W/mm², argon as the inert gas was caused to flow at a flowrate of 50 l/min, the light for 1.5 microsecond immediately after the irradiation by the laser was excluded and the subsequent emitted light signals up to 16 microseconds were integrated, the coefficient of variation was 9.0%. According to a second method of the present invention, wherein, in addition to the first method, the mode lock mechanism was additionally provided in the laser oscillator 22 and the laser output mode was fixed to $TEM_{00}$ mode, the coefficient of variation was 7.3%. According to a third method of the present invention, wherein, in addition to the first method, the background intensity was substracted, the coefficient of variation was 5.9%. According to a fourth method of the present invention, wherein, in addition to the first method, two spectrum intensities of Fe having wavelengths of 271.4 nanometers and 273.1 nanometers were monitored and the spectral line intensity of silicon (288.2 nanometers) was read only when the intensity ratio between the aforesaid two spectrum intensities are within plus-minus 5% of the preset value, the coefficient of variation was 5.3%. According to a fifth method of the present invention, wherein all of the first to fourth methods were conducted at the same time, the coefficient of variation was 3.2%. It was ascertained that each of the aforesaid five methods was improved better than the conventional method. Particularly, it was proved that, according to the fifth method, wherein all of the methods were conducted simultaneously, the coefficient of variation was greatly improved to 3.2% as compared with 11.4% of the conventional method.

What is claimed is:

1. A method of laser emission spectroscopic analysis of steel, wherein a light emitted when a laser beam irradiates the surface of the steel is spectrally separated and elements contained in the steel are quantitatively analyzed, comprising the steps of:

irradiating a sample with an infrared pulse laser beam to turn a part of said sample into plasma such that an energy density on the surface of the sample is $2.0 \times 10^9$ W/mm² or more;

receiving a light emitted from the surface of the sample by a light introducing system at a solid angle of 16 degrees or more through a path held under an atmosphere of inert gas blown into said path at a flow rate of at least 50 l/min, and thereafter forming an image on an inlet slit of a spectroscope with said light; and quantitatively analyzing said light, such that a firstly emitted portion of said light generating white noise is excluded, and a subsequently emitted portion of said light is analyzed, and an analyzed value is obtained from a spectral line intensity of an element to be measured only when an intensity of a preset spectral line or an intensity ratio between a pair of preset spectral lines is within a preset range.

2. A method as set forth in claim 1, wherein an output of said infrared pulse laser beam is fixed to a gauss distribution type $TEM_{00}$ mode.

3. A method as set forth in claim 1, wherein said firstly emitted portion of said light is of 1.5 microsecond or less duration.

4. A method as set forth in claim 1, wherein said firstly emitted portion of said light is of 1.5 microsecond or less duration, and said subsequently emitted portion of said light is of up to 16 microsecond duration.

5. A method as set forth in claim 1, wherein, in conducting said quantitative analysis, an intensity of a light having a preset wavelength emitting no spectral line is made to be a background which is substracted from said spectral line intensity.

6. A method as set forth in claim 1, wherein:
an output of said infrared pulse laser beam is fixed to a gauss distribution type $TEM_{00}$ mode; and
in conducting the quantitative analysis, a light intensity having a preset wavelength emitting no spectral light is made to be a background, which is subtracted from said spectral line intensity.

7. An apparatus for laser emission spectroscopic analysis of steel, wherein a light emitted when a laser beam irradiates the surface of the steel is spectrally separated and elements contained in the steel are quantitatively analyzed, comprising:
laser oscillating means assembled thereinto with a mode lock mechanism, for emitting an infrared pulse laser beam having an energy density of $2.0 \times 10^9$ W/mm$^2$ or more on the surface of a sample to turn a part of said sample to plasma;
a focusing mirror for focusing a light emitted from the surface of the sample at a focusing solid angle of 16 degrees or more;
a casing and means for introducing inert gas through an inert gas introducing port in said casing at a flow rate of at least 50 l/min for holding a path of said light emitted from the sample under an atmosphere of the inert gas in said casing;
spectroscopic means wherein said light emitted from the sample whose image is formed at an inlet slit of the spectroscopic means by said focusing mirror is spectrally separated into spectral lines by a diffraction means;
detecting means including a group of photoelectric signal transducing elements wherein preset spectral lines of target elements are converted into electric signals;
a spectrum intensity monitor for monitoring an intensity of a preset spectral line or an intensity ratio between a pair of preset spectral lines;
gate means to be opened during a period from 1.5 microsecond after the start of the irradiation by the laser beam up to 16 microseconds and when the intensity of the preset spectral line or the intensity ratio between the pair of preset spectral lines is within the preset range, so that an output from said spectroscopic means can be adopted in the analysis; and
signal processing means for obtaining an analyzed value in response to a signal inputted from said spectroscopic means when said gate means is opened.

* * * * *